United States Patent
Dees et al.

(10) Patent No.: US 10,188,404 B2
(45) Date of Patent: Jan. 29, 2019

(54) ORTHOPEDIC INSTRUMENTATION

(71) Applicant: Smith & Nephew, Inc., Memphis, TN (US)

(72) Inventors: Roger Ryan Dees, Senatobia, MS (US); Jeffrey N. Yeager, Nesbit, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/892,634

(22) Filed: Feb. 9, 2018

(65) Prior Publication Data

US 2018/0161044 A1 Jun. 14, 2018

Related U.S. Application Data (63) Continuation of application No. 15/746,176, filed as application No. PCT/US2016/043136 on Jul. 20, 2016.

(Continued)

(51) Int. Cl.
| | |
|---|---|
| A61B 17/00 | (2006.01) |
| A61B 17/16 | (2006.01) |
| A61B 17/17 | (2006.01) |
| A61B 90/00 | (2016.01) |

(52) U.S. Cl.
CPC ........ *A61B 17/164* (2013.01); *A61B 17/1659* (2013.01); *A61B 17/17* (2013.01); *A61B 17/1735* (2013.01); *A61B 17/1697* (2013.01); *A61B 17/1764* (2013.01); *A61B 2017/1602* (2013.01); *A61B 2090/062* (2016.02)

(58) Field of Classification Search
CPC ..... A61B 17/15; A61B 17/16; A61B 17/1615; A61B 17/1622; A61B 17/164

(Continued)

(56) References Cited

U.S. PATENT DOCUMENTS

| | | | | |
|---|---|---|---|---|
| 3,524,227 A | * | 8/1970 | Kelly | .................... F16G 11/101 24/115 R |
| 2013/0150858 A1 | | 6/2013 | Primiano et al. | |
| 2013/0172892 A1 | | 7/2013 | Servidio et al. | |

FOREIGN PATENT DOCUMENTS

| | | |
|---|---|---|
| DE | 2542056 A1 | 3/1977 |
| DE | 102004043315 A1 | 3/2004 |

(Continued)

OTHER PUBLICATIONS

International Search Report; European Patent Office; International Application No. PCT/US2016/043136; dated Jan. 11, 2017; 7 pages.

(Continued)

*Primary Examiner* — Si Ming Ku
(74) *Attorney, Agent, or Firm* — Taft Stettinius & Hollister LLP (57) ABSTRACT

An instrumentation system that includes a reamer sleeve having a reamer wall and a wedge body, the reamer wall being oriented about a central longitudinal axis. The reamer wall includes an inner passage that is sized to receive insertion of a reference instrument that is structured for placement in a canal in a bone. The inner passage can be centrally oriented about a longitudinal axis that is offset from at least the central longitudinal axis of the reamer wall. The wedge body can have a wedge surface that extends axially in a direction that is non-parallel and non-perpendicular to the central longitudinal axis. The apparatus also can include a cap having an opening that is sized to receive insertion of the wedge body. The cap can further include an inner wall having a tapered wall section that is oriented to matingly engage the wedge surface of the wedge body.

20 Claims, 8 Drawing Sheets

Related U.S. Application Data (60) Provisional application No. 62/195,035, filed on Jul. 21, 2015.

(58) Field of Classification Search
USPC .............................................. 606/80, 87, 88
See application file for complete search history.

(56) References Cited

FOREIGN PATENT DOCUMENTS

| | | | |
|---|---|---|---|
| EP | 2431008 | A1 | 3/2012 |
| WO | 9427507 | A1 | 12/1994 |
| WO | 9842280 | A1 | 10/1998 |

OTHER PUBLICATIONS

Written Opinion of the International Searching Authority; European Patent Office; International Application No. PCT/US2016/043136; dated Jan. 11, 2017; 8 pages.

DePuy International Ltd.; LCS Complete Revision Surgical Technique; May 2010; 60 pages.

Smith & Nephew, Inc.; Genesis II Revision Surgical Technique; Jul. 2002; 40 pages.

Biomet Orthopedics; Regenerex Tibial Cone Augment Surgical Technique Addendum to the Vanguard SSK Revision System; 2009; 12 pages.

Zimmer, Inc.; Zimmer Trabecular Metal Tibial and Femoral Cones Surgical Techniques, 2011; 44 pages.

\* cited by examiner

ORTHOPEDIC INSTRUMENTATION

CROSS REFERENCE TO RELATED APPLICATIONS

The present application is a continuation of U.S. patent application Ser. No. 15/746,176 filed on Jan. 19, 2018, which is a U.S. National Phase of International PCT Application No. PCT/US2016/043136 filed on Jul. 20, 2016, which claims the benefit of U.S. Provisional Patent Application Ser. No. 62/195,035 filed Jul. 21, 2015, the contents of each application hereby incorporated by reference in their entirety.

BACKGROUND

Embodiments of the present invention generally relate to as instrumentation system for preparation for implantation of a metaphyseal and/or diaphyseal implant or augment. More particularly, but not exclusively, embodiments of the present invention relate to instrumentation that facilitates a degree of positional freedom in the placement of a metaphyseal and/or diaphyseal implant or augment relative to a inference axis.

Proper alignment of a replacement joint device, including components of the replacement joint device, often may at least assist in attaining optimal wear resistance and optimal performance of the implanted device. Yet, patient anatomical variations present challenges in properly aligning the implant device for each patient. For example, during implant construct of knee replacement joints, challenges may arise with fitting a patient's intramedullary geometry with an implant, such as, for example, an intramedullary stem, while also fitting both the external geometry with a condylar replacing implant and the metaphyseal and/or diaphyseal geometry with an associated implant or augment component. Moreover, the addition of a metaphyseal and/or diaphyseal implant or augment to an implant construct often impairs the ability to adjustably fit the implant to the patient and/or attain proper alignment for various components of the implant. Such difficulties may at times be attributed to the anatomy of the patient, the geometrical constraints of the implant, and/or constraints associated with the preparatory instrumentation. For example, geometrical constraints of the metaphyseal and/or diaphyseal implant or augment may include the inability of the implant to accommodate the placement or position of both the intramedullary stem and the condylar implant, which can attribute to difficulties in forming a junction mechanism for those, and possibly other, components of the implant.

Challenges associated with attaining proper alignment during implant construct that involves metaphyseal and/or diaphyseal implants or augments have, at times, been resolved by compromises in terms of the placement of at least some components of the implant device, such as, for example, the location of the condylar implant. Yet, such compromises can result in less than optimal bone coverage, which can potentially compromise loading of the construct to the cortical rim of the bone. Other compromises can include reducing the stem size in order to offset the stem position, with the area vacated by such offsetting being made up with cement. Yet, for various reasons, such compromises may already impact the life of the implant, including being associated with failures relating to subsidence, loosening, stress-shielding factors, and increased stresses on the implant device, among other failures. Therefore, the integrity of the implant construct may be adversely impacted if the bone is not shaped, during implant surgery, to accommodate the positioning of augmenting implants at locations in which the implanted augments, such as, for example, stems, sleeves, and cones, among other augments, will not interfere with the articular component and/or other augmenting implants.

BRIEF SUMMARY

Certain embodiments of the invention may include an apparatus that includes a reamer sleeve having a reamer-wall and a wedge body, the reamer wall being oriented about a central longitudinal axis. The reamer wall includes an inner passage that is sized to receive insertion of a reference instrument that is structured for placement in a canal of a bone. The wedge body can extend from a first end wall of the reamer wall and can have a wedge surface that extends axially in a direction that is non-parallel and non-perpendicular to the central longitudinal axis. The apparatus can also include a cap having an inner wall, at least a portion of the inner wall defining an opening of the cap that is sized to receive insertion of the wedge body. Additionally, the inner wall can have a tapered wall section that extends axially in a direction that is generally parallel to the wedge surface.

Certain embodiments of the invention may also include a reamer sleeve that is adapted to be positioned about a reference instrument. The reamer sleeve can include an inner passage and a wedge body, the inner passage being sized to receive insertion of the reference instrument. The wedge body can extend from a first end wall of a reamer wall of the reamer sleeve and can include an inner surface and a wedge surface at opposing sides of the wedge body. The inner surface of the wedge body can be positioned to abut against a portion of the inserted reference instrument, while the wedge surface can be oriented on an incline that is non-parallel and non-perpendicular to the inner surface.

Additionally, certain embodiments of the invention may include a cap for placement about a reamer sleeve. The cap can include a cap wall having an inner side and an outer side, the inner side structured to abut against the reamer sleeve. Further, the inner side can define an opening that axially extends about a central axis. Additionally, the inner side can have a tapered wall section that extends along an incline in a direction that is non-parallel and non-perpendicular to the central axis. The cap can also include a spline tooth, at least a portion of the spline tooth extending into the opening.

BRIEF DESCRIPTION OF THE DRAWINGS

The description herein makes reference to the accompanying figures wherein like reference numerals refer to like parts throughout the several views.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DESCRIPTION OF THE ILLUSTRATED EMBODIMENTS

Certain terminology is used in the foregoing description for convenience and is not intended to be limiting. Words such as "upper," "lower," "top," "bottom," "first," and "second" designate directions in the drawings to which reference is made. This terminology includes the words specifically noted above, derivatives thereof, and words of similar import. Additionally, the words "a" and "one" are defined as including one or more of the referenced item unless specifically noted. The phrase "at least one of" followed by a list of two or more items, such as "A, B or C," means any individual one of A, B or C, as well as any combination thereof.

Figure 1:
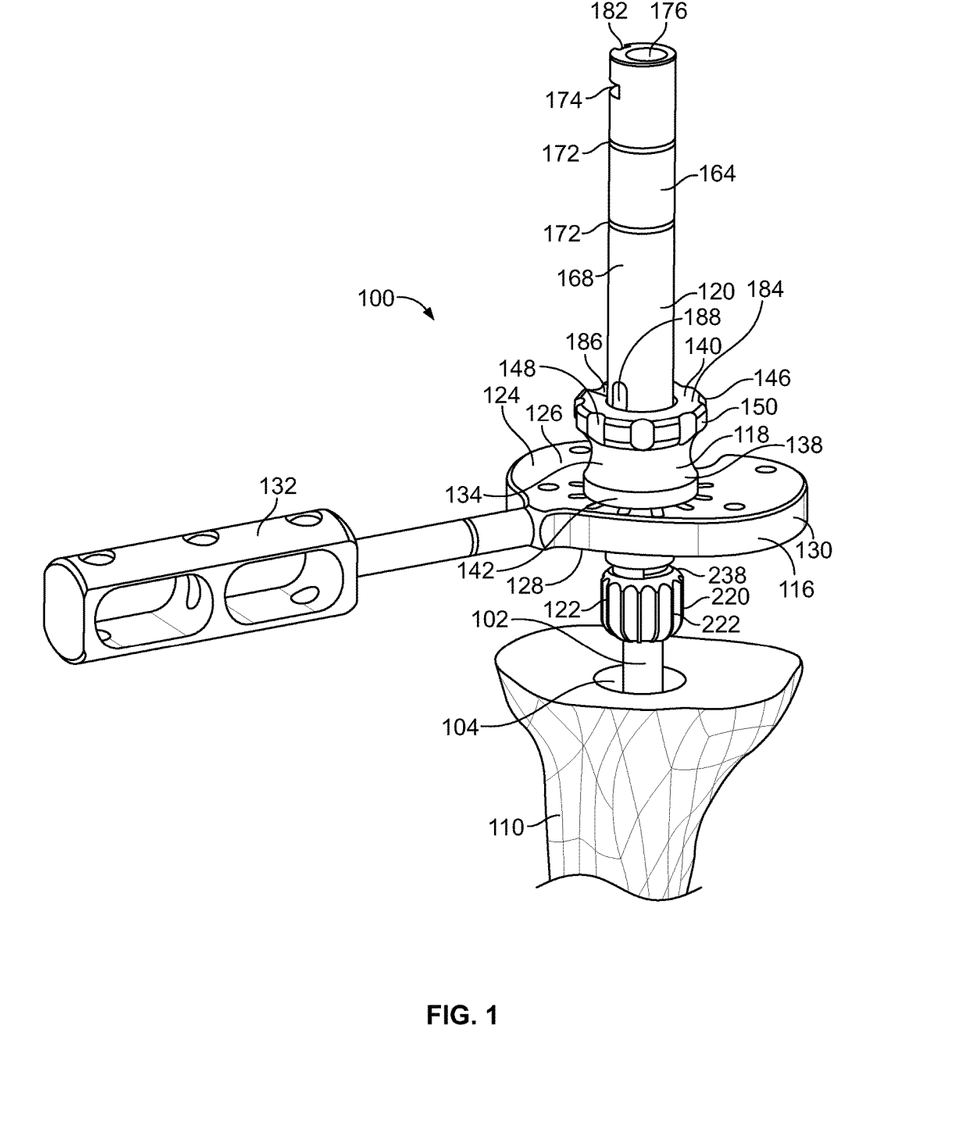
FIG. 1 illustrates a side perspective view of an exemplary orthopedic instrumentation system positioned about a portion of a reference instrument according to an illustrated embodiment of the present invention.
Figure 2:
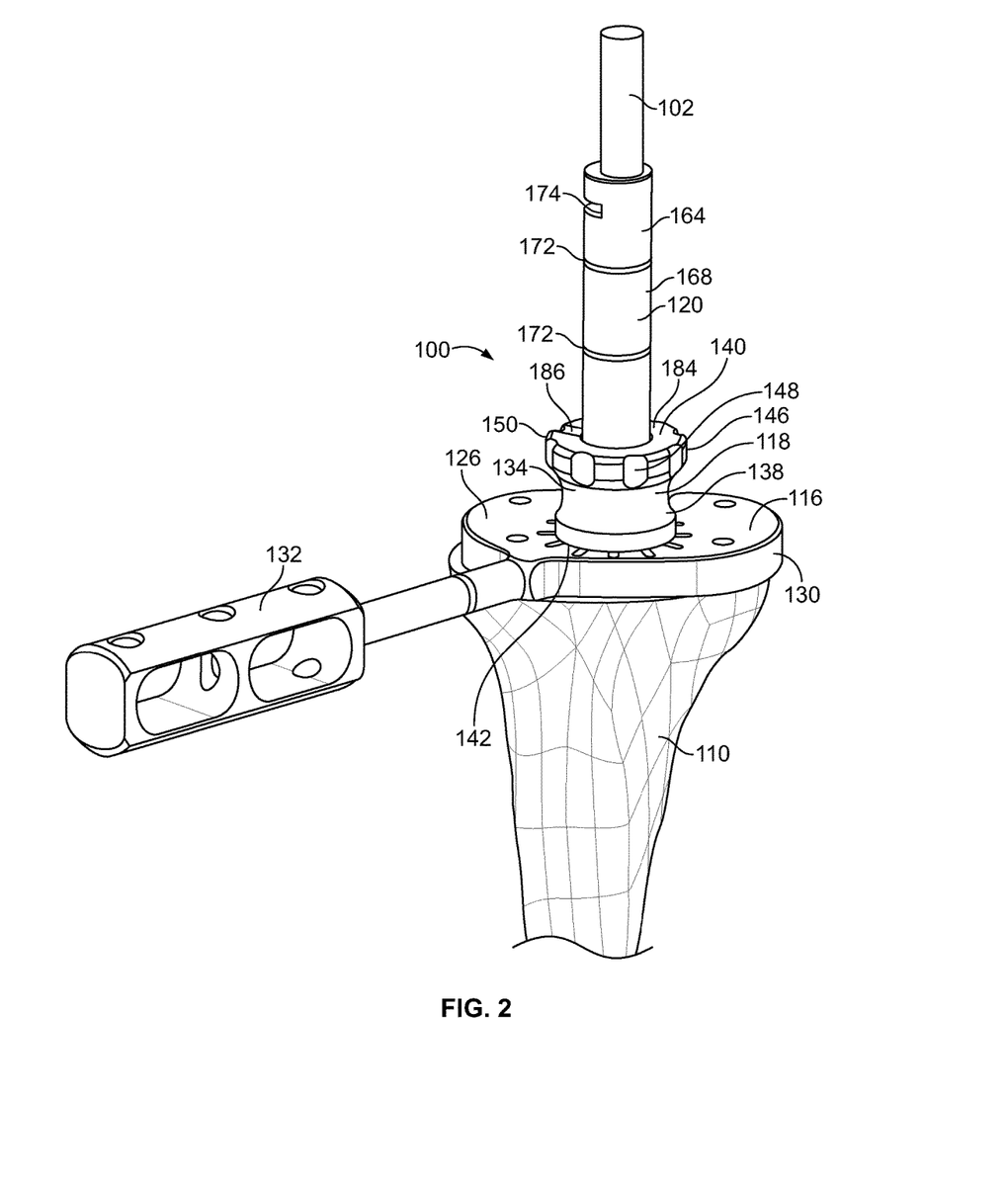
FIG. 2 illustrates a side perspective view of the orthopedic instrumentation system of FIG. 1 positioned about a portion of the reference instrument, and with a portion of the orthopedic instrumentation system at a wedged position in an intramedullary canal of a bone.
Figure 3:
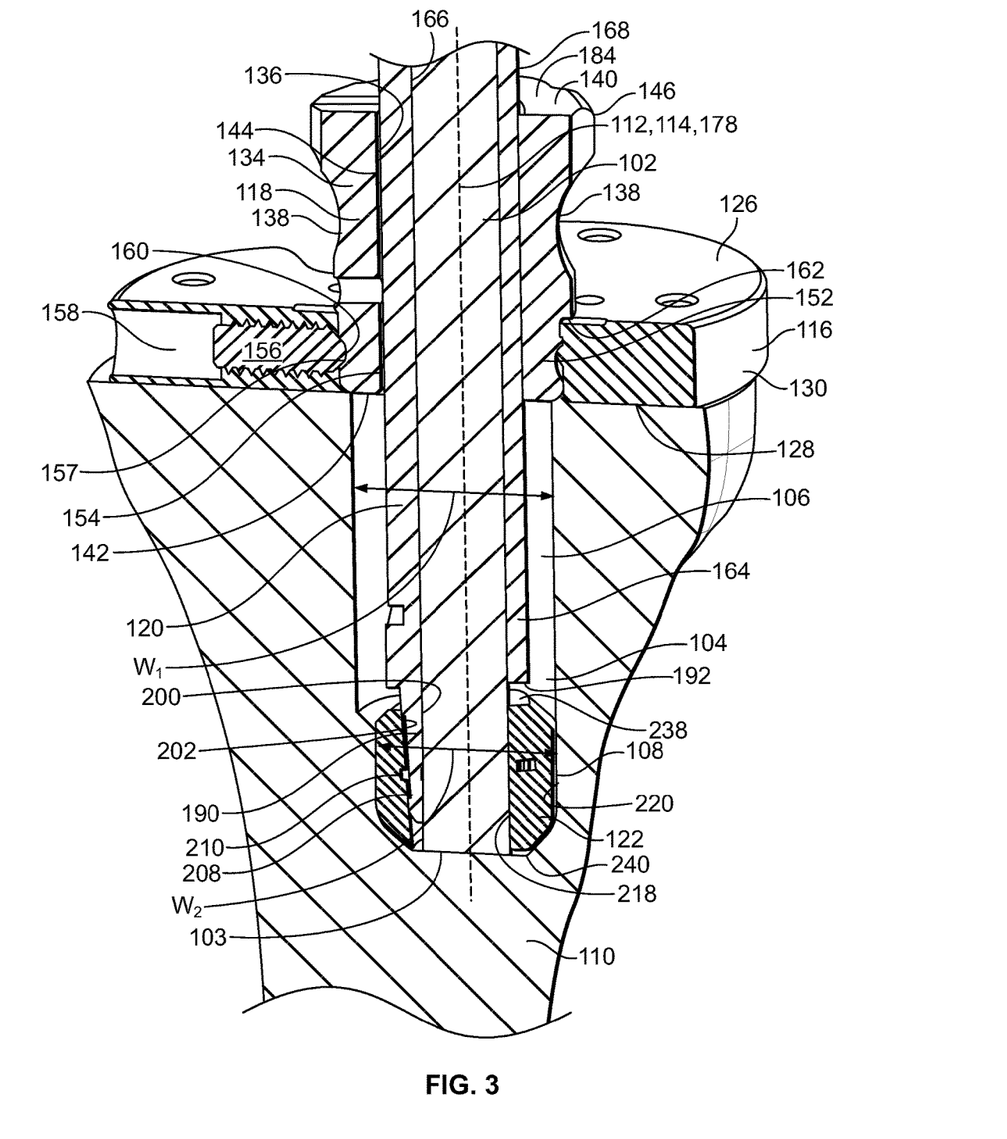
FIG. 3 illustrates a side cross-sectional view of a portion of the orthopedic instrument system shown in FIG. 2 at the wedged position relative to the canal of the bone.

FIGS. 1-3 illustrate side perspective and cross sectional views of an exemplary orthopedic instrumentation system 100 positioned about a portion of a reference instrument 102 according to an illustrated embodiment of the present invention. Referencing FIG. 3, at least a portion of the reference instrument 102 can be structured to be positioned in an intramedullary canal 104 of a bone 110. According to certain embodiments, the intramedullary canal 104 in which the reference instrument 102 is placed can include a prepared portion which can comprise an area or segment in the bone 110 in which the size of the intramedullary canal 104 was increased by a surgical preparatory procedure, such as reaming or drilling, among other bone removal procedures. For example, in the embodiment depicted in FIG. 3, the width, such as diameter, of a portion of the intramedullary canal 104 that can be increased to a first width (as indicated by "$w_1$" in FIG. 3) to provide a prepared portion 106 of the intramedullary canal 104. According to such an example, the first width of the prepared portion 106 of the intramedullary canal 104 can be larger than a corresponding second width (as indicated by "$w_2$" in FIG. 3) of other, non-prepared portions 108 of the intramedullary canal 104, such as portions of the intramedullary canal 104 that were not subjected to the surgical preparatory procedure.

At least a portion of the intramedullary canal 104 can be generally located about a central location the intramedullary canal 104. Further, the central longitudinal axis 112 of the intramedullary canal 104 may or may not be at a generally central location along the prepared portion 106 of the intramedullary canal 104. For example, in the embodiment shown in FIG. 3, the prepared portion of the intramedullary canal 104 is offset from the non-prepared portion 106 of the intramedullary canal 104. Thus, in at least certain situations, the central longitudinal axis 112 of the intramedullary canal 104 can be positioned at a generally central position relative to the non-prepared portion 108 of the intramedullary canal 104, while the prepared portion 106 of the intramedullary canal 104 is generally at an offset position relative to the central longitudinal axis 112.

A variety of different types of instruments or guides can be utilized for the reference instrument 102, including, for example, an intramedullary rod, trial stem, reamer, or offset rod, among other instruments or guides. According to certain embodiments, the reference instrument 102 extends along a central longitudinal axis 114. Further, when positioned in the intramedullary canal 104, the central longitudinal axis 114 of the reference instrument 102 may, or may not, generally extend along the central longitudinal axis 112 of the canal 104, as demonstrated in FIG. 3. Additionally, according to certain embodiments at least a portion of a first end of the reference instrument 102 can be structured to be affixed in the intramedullary canal 104 of the bone 110. Moreover, according to certain embodiments, the first end 103 of the reference instrument 102 can be secured to the bone 110 in or adjacent to the non-prepared portion 108 of the intramedullary canal 104.

The orthopedic instrumentation system 100 can include a guide 116, guide bushing 118, reamer sleeve 120, and cap 122. The guide 116 can include a body portion 124 having opposing first and second sides 126, 128 and an edge 130 that generally define an outer periphery of the body portion 124. The guide 116 can also include a handle 132 that outwardly extends from the body portion 124. The handle 132 can be structured to at least assist in the positioning and/or maintaining a position of at least the body portion 124 of the guide 116 relative to the bone 110 and/or intramedullary canal 104. According to certain embodiments, the guide 116 can be a drill guide or tray profile instrument. Further, according to certain embodiments the handle 132 can be removably coupled to the body portion 124, such as, for example, by a mating threaded connection.

The guide bushing 118 can include a wall 134 having an inner portion 136 and an outer portion 138, and that extends between a second end 140 and a first end 142 of the guide bushing 118. The inner portion 136 of the wall 134 can generally define a bushing aperture 144 of the guide bushing 118 that is sized to receive insertion of at least a portion of the reamer sleeve 120. For example, the bushing aperture 144 of the guide bushing 118 can have a size, such as, for example, a diameter, that can receive the placement of at least a portion of the reamer sleeve 120 in a manner that accommodates the axial displacement or sliding of the reamer sleeve 120 along the bushing aperture 144, or vice versa, while also minimizing the degree, if any, to which the reamer sleeve 120 can be transversally displaced within the bushing aperture 144.

The second end 140 of the guide bushing 118 can include an engagement portion 146 that is shaped or configured to facilitate the ability to grip or otherwise manipulate the position of the guide bushing 118. Moreover, the engagement portion 146 can improve a grasp on the guide bushing 118 at least when an angular position of the guide bushing 118 is adjusted, such as, for example, an adjustment of the angular position of at least the guide bushing 118 member relative to at least the intramedullary canal 104 and/or the guide 116. For example, according to the illustrated embodiment, a portion of the outer portion 138 of the wall 134 of the guide bushing 118 can include a plurality or recesses 148 intermixed with a plurality of projections 150 that are structured to enhance the ability of a user to grasp, and/or retain a grasp of, the guide bushing 118. According to other embodiments, the engagement portion 146 can comprise at least a knurled surface along at least a portion of the outer portion 138 of the wall 134.

The guide bushing 118 is configured to be coupled to the guide 116. For example, according to certain embodiments, at least a portion of the outer portion 138 of the wall 134 at the first end 142 of the guide bushing 118 provides an end portion 152 that is configured to be received in the aperture 154 of the guide 116. Further, the end portion 152 of the wall 134 and the aperture 154 of the guide 116 can be configured to minimize the degree, if any, to which the end portion 152 can be transversally displaced within the aperture 154 of the guide 116. Further, the guide bushing 118 can be coupled to the guide 116 by at least one mechanical fastener 156, such as, for example, a pin, screw, bolt, or clip, among other mechanical fasteners. For example, as shown in FIG. 3, according to the depicted embodiment, the fastener 156 can be a ball plunger that threadingly engages at least a threaded portion of an orifice 158 in the guide 116. Further, in the depicted embodiment, the orifice 158 is in communication with the aperture 154 of the guide 116 such that the fastener 156 can be displaced via the threaded engagement with the office 158 to a position in which an end segment 157 of the fastener 156 exerts a force against a portion of the end portion 152 of the guide bushing 118. Optionally, according to certain embodiments, rotational displacement or tightening of the fastener 156 can result in the end segment 157 of the fastener 156 exerting a force against the guide bushing 118 that prevents rotational displacement of the guide bushing 118 relative to at least the guide 116.

In the depicted embodiment, the end portion 152 of the wall 134 of the guide bushing 118 includes recessed section 160 that can be configured to facilitate engagement between the fastener 156 and the end segment 157 of the fastener 156. For example, in the depicted embodiment, the recessed section 160 includes a radius or opposing angled surfaces that generally mate the radius or configuration at the end segment 157 of the fastener 156. According to certain embodiments, the recessed section 160 can be positioned to generally align with the orifice 158 of the guide 116, and thus the fastener 156, when a bottom wall 134 at the first end 142 of the guide bushing 118 is positioned against a portion of the bone 110, as shown for example in FIG. 3. Alternatively, the recessed section 160 of the guide bushing 118 can generally align with the orifice 158 when a shoulder portion 162 of the wall 134 of the bushing guide 116 abuts against the first side 126 of the guide 116, as shown for example in FIGS. 1-3.

The reamer sleeve 120 includes a reamer wall 164 having an inner side 166 and an outer side 168. According to the illustrated embodiment, at least the outer side 168 of the reamer wall 164 can extend about a central longitudinal axis 170. Further, the outer side 168 of the reamer wall 164 is configured to be axially displaced along the bushing aperture 144 of the bushing guide 116, or vice versa, as previously discussed. Thus, the outer side of the reamer wall 164 can have a shape and/or size that generally conforms to the shape and/or size of the bushing aperture 144.

Referencing FIGS. 1 and 2, according to the illustrated embodiment, the outer side 168 of the reamer wall 164 can include one or more depth indicators 172. Such depth indicators 172 can provide an indication of the depth to which the reamer sleeve 120 has been inserted into an opening in the bone 110. Further, according to certain embodiments, one or more of the depth indicators 172 can provide an indication of a minimum depth that the reamer sleeve 120 is to be inserted into an opening in the bone 110. The reamer sleeve 120 can also include a recess 174 that extends through the outer side 168 and which is configured to assist in removal of the reamer sleeve 120 from the bone 110 and/or guide bushing 118. For example, the recess 174 can be sized to receive a portion of a slide hammer that assists in removal of the reamer sleeve 120 from the bone 110 or guide bushing 118.

The inner side 166 of the reamer sleeve 120 can generally define an inner passage 176 that is configured to receive insertion of at least a portion of the reference instrument 102. Moreover, the inner passage 176 can have a cross sectional size and/or shape that is similar to that of the reference instrument 102. For example, according to certain embodiments, the inner passage 176 can have a size that accommodates axial displacement of the reamer sleeve 120 along the reference instrument 102 and which also limits the extent, if any, that the reamer sleeve 120 can be transversely displaced about the received reference instrument 102.

Figure 8:
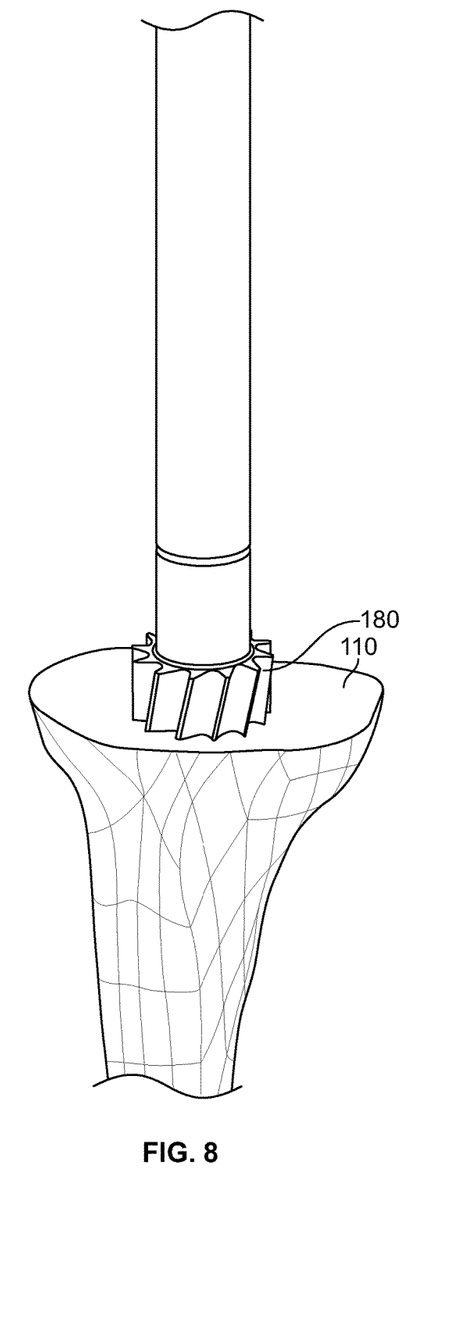
FIGS. 8 and 9 illustrate a side perspective view and a partial cutaway view, respectively, of the forming tool of FIG. 7 positioned about the reamer sleeve of the orthopedic instrument system and a corresponding formed portion of the canal of the bone.

As shown in FIGS. 4A-4E, the inner passage 176 can extend along a longitudinal axis 178. When the reamer sleeve 120 is positioned about the reference instrument 102, the longitudinal axis 178 of the inner passage 176 can generally align with the central longitudinal axis 114 of the reference instrument 102. Additionally, the longitudinal axis 178 of the inner passage 176 may, or may not, be offset from a central longitudinal axis 170 of the reamer sleeve 120. Such similarities and/or differences in the relative positions of the longitudinal axis 178 of the inner passage 176 and the central longitudinal axis 170 of the reamer sleeve 120 can allow for adjustment in the position of the forming tool 180 (FIGS. 8-10) relative to one or more reference axis(es), such as, for example, the central longitudinal axis 114 of the reference instrument 102 and/or the central longitudinal axis 112 of the intramedullary canal 104, as discussed below. Moreover, as discussed below, as the forming tool 180 can be generally centrally positioned about the reamer sleeve 120, adjustments in the position of the central longitudinal axis 170 of the reamer sleeve 120 relative to the longitudinal axis 178 of the inner passage 176 can adjust the position at which the forming tool 180 removes bone material relative to the central longitudinal axis 112 of the intramedullary canal 104 and/or the central longitudinal axis 114 of the reference instrument 102.

Figure 4A:
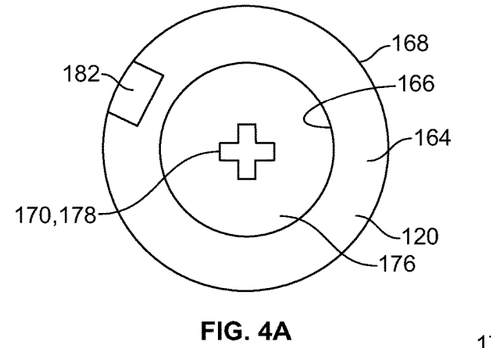
FIGS. 4A-E illustrate offset and non-offset positions of inner passages of exemplary reamer sleeves relative to a central axis of the associated reamer sleeve according to illustrated embodiments of the present invention.

As shown in FIG. 4A, according to certain embodiments, the longitudinal axis 178 of the inner passage 176 can generally align with the central longitudinal axis 170 of the reamer sleeve 120. Moreover, as previously discussed, in such situations, the central longitudinal axis 170 of the reamer sleeve 120 can be generally aligned with a reference axis, such as the central longitudinal axis 112 of the intramedullary canal 104, the central longitudinal axis 114 of the reference instrument 102, and/or longitudinal axis 178 of the inner passage 176. Thus, in such situations, and as discussed below, bone material that is subsequently removed from the bone 110 by operation of the forming tool 180 can generally be located at a position in the bone 110 that is generally aligned with the central longitudinal axis 170 of the reamer sleeve 120, as well as the central longitudinal axis 112 of the intramedullary canal 104, the central longitudinal axis 114 of the reference instrument 102, and/or the longitudinal axis 178 of the inner passage 176.

Figure 4B:
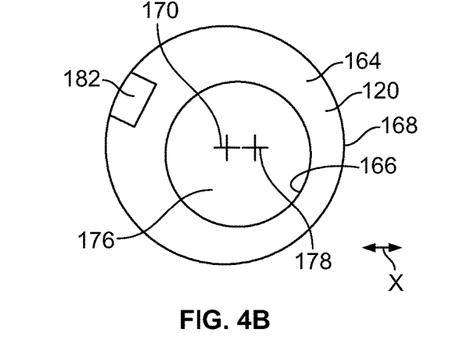
Figure 4C:
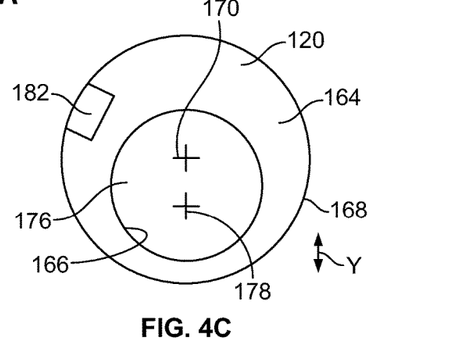

According to other embodiments, the position of the longitudinal axis 178 of the inner passage 176 can be offset from the central longitudinal axis 170 of the reamer sleeve 120 along a first axis (as indicated by the "X" direction in FIG. 4B) and/or a second axis (as indicated by the "Y" direction in FIG. 4C). Further, the longitudinal axis 178 of the inner passage 176 can be offset from the central longitudinal axis 170 of the reamer sleeve 120 in directions that are a combination of these two axes (e.g., "X" and "Y" axes in FIGS. 4B and 4C, respectively), among other axes, as shown for example by FIG. 4D. Such freedom can allow for the forming tool 180 to form an opening, or formed portion, in the bone 110 at a location that can improve the alignment of the subsequently implanted orthopedic device and/or prevent an implanted augment from touching another component of the implant device, such as, for example, an augment touch a tibial stem or a tray stem that extends from a tibial tray.

Figure 4D:
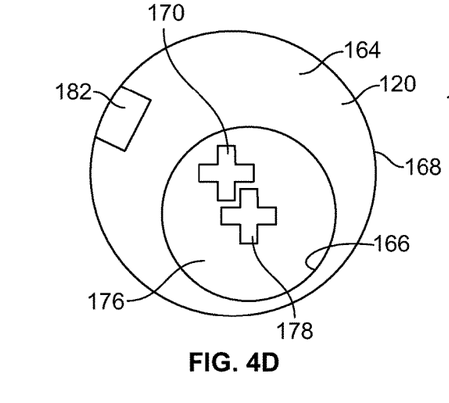
Figure 4E:
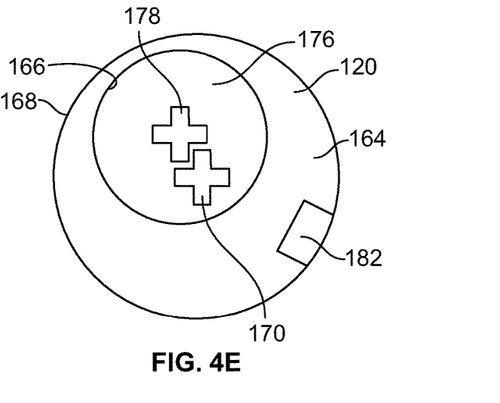

In addition to displacement along at least two axes, such as, for example, along the "X" and "Y" axes shown in FIGS. 4B and 4C, respectively, and/or a combination thereof, according to certain embodiments, the inner passage 176 of the reamer sleeve 120 can also allow for at least a degree of adjustment or displacement in the angular orientation of the reamer sleeve 120 about the reference instrument 102, as indicated, for example, by a comparison of FIGS. 4D and 4E. In at least certain situations in which the longitudinal axis 178 of the inner passage 176 is offset from the central longitudinal axis 170 of the reamer sleeve 120, such angular displacement can allow at least adjustment in the location of the longitudinal axis 178 of the inner passage 176 relative to at least the central longitudinal axis 112 of the intramedullary canal 104, and thereby adjust the location at which the forming tool 180 forms the formed portion in the bone 110. According to certain embodiments, the angular orientation of the central longitudinal axis 170 of the reamer sleeve 120 can be adjusted around 360 degrees relative to at least the location of the longitudinal axis 178 of the inner passage 176 and the central longitudinal axis 112 of the intramedullary canal 104.

As shown by FIGS. 1 and 4A-4E, the outer side 168 of the reamer sleeve wall 164 can include an orientation indicator 182 that assists in providing an indication of the rotational position of at least the reamer sleeve 120. The orientation indicator 182 of the reamer sleeve 120 can take a variety of forms, including, for example being a slot, groove(s), recess, or protrusion. Further, according to certain embodiments, the orientation indicator 182 of the reamer sleeve 120 can form or be provided with or as indicia, such as a shape(s), letter(s), and/or number(s) that provides an indication of the angular position of at least the reamer sleeve 120. Additionally, according to certain embodiments, an upper wall 184 of the guide bushing 118 can also include an orientation indicator 186 that can generally align with the orientation indicator 182 of the reamer sleeve 120. For example, as shown in FIGS. 1 and 3, the orientation indicator 186 of the guide bushing 118 can be a slot, recess, groove, and/or indicium, such as a shape, that provides an indication of the angular orientation of at least the reamer sleeve 120. According to certain embodiments, the orientation indicators 182, 186 of the reamer sleeve 120 and the guide bushing 118 can be generally aligned by alignment of keyways of the reamer sleeve 120 and the guide bushing 118. Further, according to certain embodiments, the orientation indicator 182 of the reamer sleeve 120 can be a keyway that, when aligned with a keyway of the guide bushing 118, is generally aligned with the orientation indicator 186 of the guide bushing 118. Further, according to certain embodiments, the orientation indicators 182, 186 of the reamer sleeve 120 and the bushing guide 116 can generally be rotated to align with different angular position indicators, for example, numbers, among other angular position indicators, that are arranged on the first side 126 of the guide 116.

The outer side 168 of the reamer sleeve 120 can also include a relief 188 that can provide a location for information identifying the reamer sleeve 120. For example, the relief 188 can provide a location at which the part number of the reamer sleeve 120 and/or information regarding the offset, if any, provided by the longitudinal axis 178 of the inner passage 176, among other information. The relief 188 can be recessed in the other side 168 of the reamer sleeve 120 so as to at least attempt to prevent damage to the relief 188 that could adversely impact the information contained in the relief 188. For example, the relief 188 can have a depth into the reamer sleeve 120 that positions information in the relief 188 at a location that can prevent that information from being removed or adversely effected by wear or usage of the reamer sleeve 120.

Figure 5:
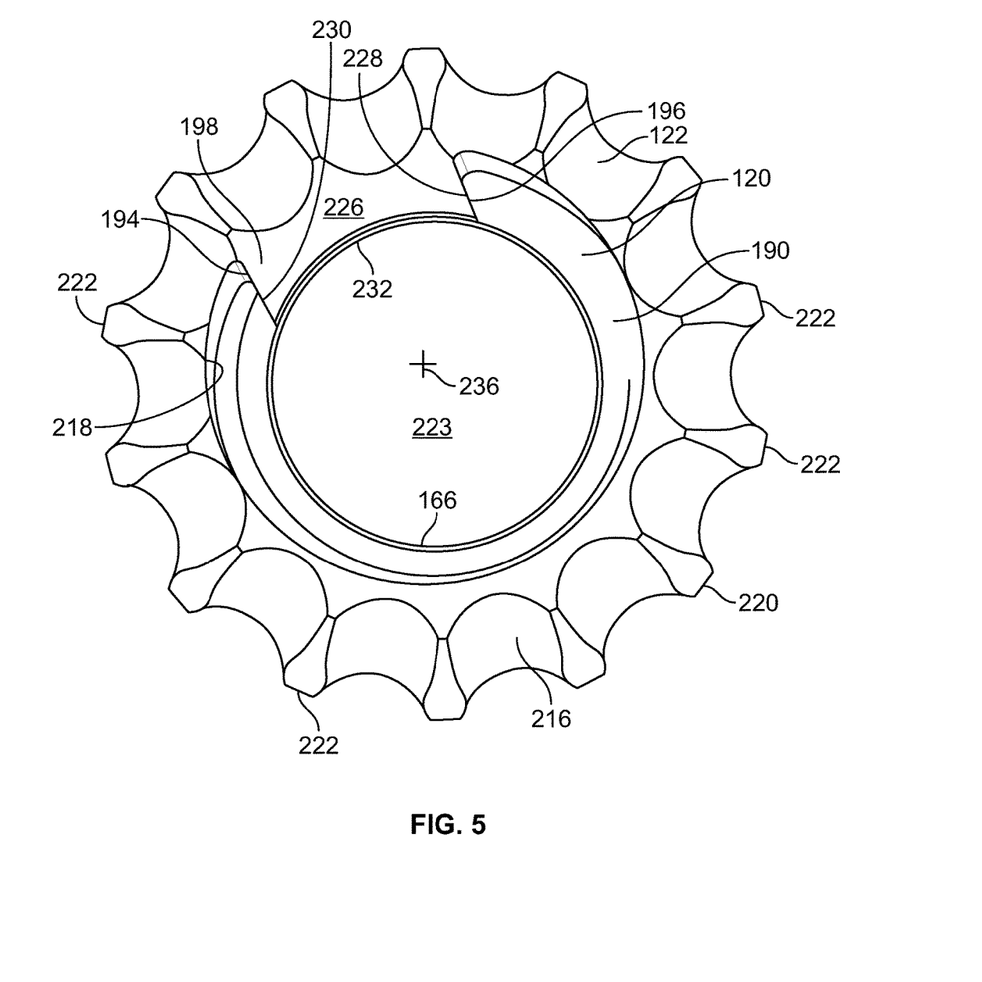
FIG. 5 illustrates an end view of a cap positioned about a reamer sleeve according to an illustrated embodiment of the present invention.

Referencing FIGS. 3, 5, 6A, and 6B, the exemplary reamer sleeve 120 can further include a wedge body 190 that extends from a first end wall 192 of the reamer sleeve wall 164. The wedge body 190 can be configured to extend around at least a portion, if not all, of an adjacent section of the reference instrument 102. For example, according to certain embodiments, as indicated by FIG. 5, the wedge body 190 circumferentially extends between first and second sidewalls 194, 196 of the wedge body 190, the first and second sidewalls 194, 196 being separated by an axially extending slot 198. Additionally, according to certain embodiments, the wedge body 190 can include an inner surface 200 that generally has a similar configuration as the inner side 166 of the reamer sleeve 120. Moreover, the inner surface 200 of the wedge body 190 is configured to abut against an adjacent surface of the reference instrument 102. Thus, according to the illustrated embodiment, the inner surface 200 of the wedge body 190 can axially extend in a direction that is generally parallel to the central longitudinal axis 170 of the reamer sleeve 120.

The wedge body 190 can further include a wedge surface 202 that is tapered or angled relative to at least the inner surface 200 of the wedge body 190. Moreover, as shown by at least FIGS. 6A and 6B, in the illustrated embodiment, the wedge surface 202 of the wedge body 190 axially extends in a direction that is non-parallel to the central longitudinal axis 170 of the reamer sleeve 120. Thus, the wedge body 190 can generally have a thickness between the inner and wedge surfaces 200, 202 at a first end 206 of the wedge body 190 that is less than a corresponding thickness between the inner and wedge surfaces 200, 202 at a second end 204 of the wedge body 190.

Figure 6A:
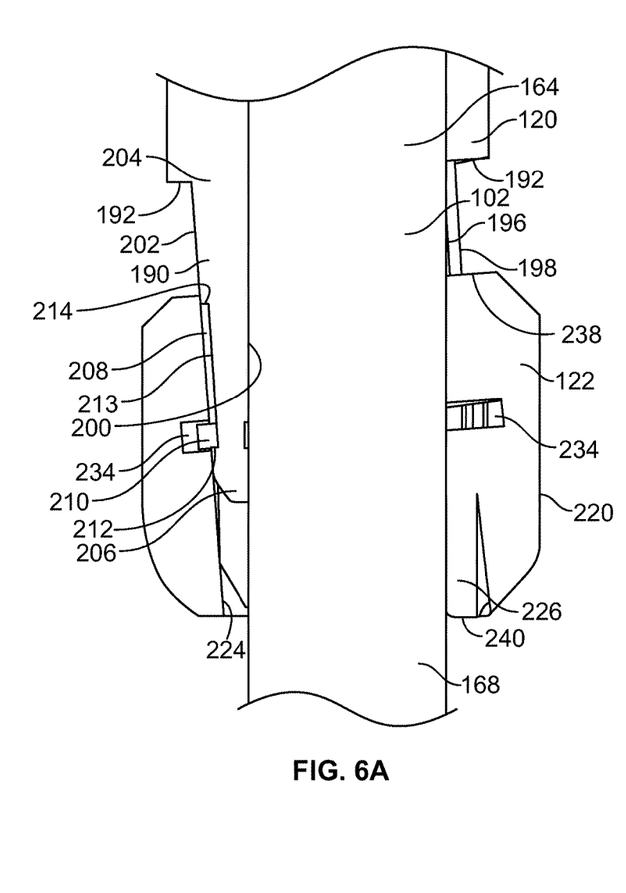
FIGS. 6A and 6B illustrate side views of a portion of an orthopedic instrument system at a first, non-wedged position and a second, wedged position, respectively, about a reference instrument.
Figure 6B:
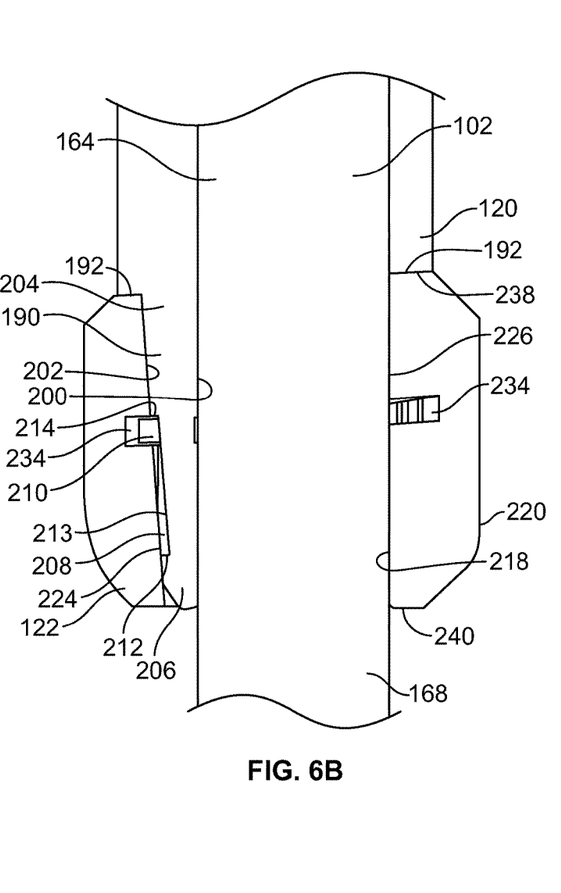
Figure 7:
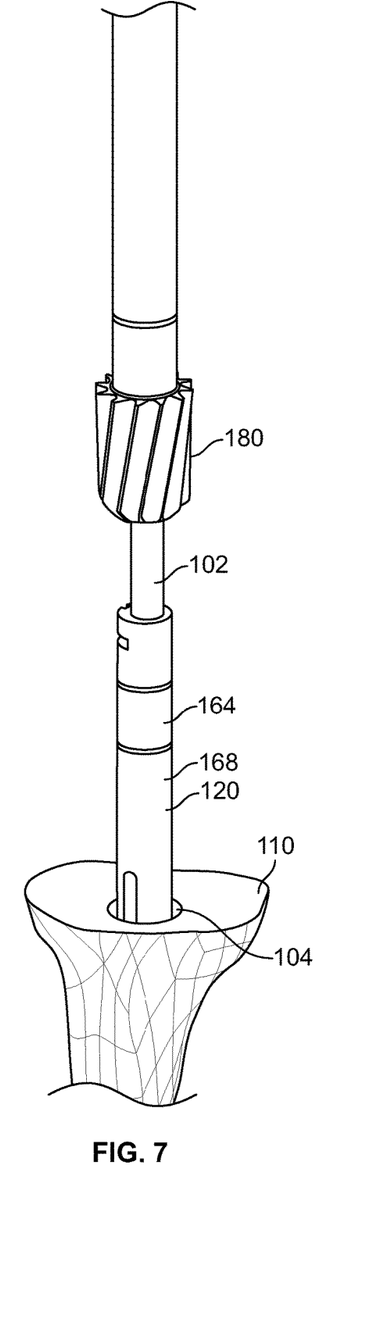
FIG. 7 illustrates a side perspective view of a forming tool positioned about a reference instrument prior to a forming tool being positioned about a reamer sleeve of an orthopedic instrument system that is extending into a canal of a bone.

According to certain embodiments, a first end wall 192 of the reamer sleeve wall 164 can extend at an incline that is generally perpendicular to the axial direction of wedge surface 202, as shown for example in FIGS. 6A and 6B. According to such an embodiment, this portion of the first end wall 192 of the reamer sleeve 120 is non-perpendicular, and non-parallel to the central longitudinal axis 170 of the reamer sleeve 120 and/or the longitudinal axis 178 of the inner passage 176.

The wedge surface 202 of the wedge body 190 can also include a cavity 208 that is configured to accommodate displacement of at least the wedge body 190 relative to a retainer 210 of the cap 122, as discussed below. The cavity 208 can extend between first and second shoulders 212, 214 of the cavity 208. The first and second shoulders 212, 214 can extend from a base wall 213 of the cavity 208 by a length that accommodates slideable displacement of the retainer 210 within the cavity 208, and which can also assist in retaining the retainer 210 within the cavity 208. Further, according to certain embodiments, the cavity 208, and thus the first and second shoulders 212, 214, can extend along the wedge body 190 at an angle that is generally perpendicular to the angle of orientation of the wedge surface 202.

The cap 122 includes a cap wall 216 having an inner side 218 and an outer side 220. The outer side 220 can be configured for placement against a bone 110 when the cap 122 is positioned within the intramedullary canal 104 and/or in a prepared opening in the bone 110. According to certain embodiments, the outer side 220 is configured to enhance the engagement between the outer side 220 of the cap 122 and adjacent bone material. For example, according to certain embodiments, the outer side 220 of the cap wall 216 includes a plurality of protrusions 222 or a knurled surface that engages the adjacent bone surface in a manner that can assist in preventing displacement of the cap 122. According to other embodiments, the protrusions 222 can deform or be compressed when the cap 122 is operably positioned in the intramedullary canal 104 or a prepared opening such that the cap 122 is subjected to a force by adjacent bone material that at least assists in preventing displacement of the cap 122.

The inner side 218 of the cap 122 generally defines an opening 223 of the cap 122 that is sized to receive insertion of at least the wedge body 190 of the reamer sleeve 120 and the reference instrument 102. Further, at least a portion of the inner side of the cap wall 216 includes a tapered wall section 224 that is configured to matingly engage the wedge surface 202 of the wedge body 190. Thus, in the illustrated embodiment, the tapered wall section 224 has an angular orientation similar to that of the wedge surface 202. Thus, when the cap 122 is operably position about the reamer sleeve 120, the tapered wall section 224 is non-parallel to the central longitudinal axis 170 of the reamer sleeve 120.

According to the illustrated embodiment, the cap 122 includes a spline tooth 226 that extends into at least a portion of the opening 223 of the cap 122. The spline tooth 226 is sized for placement within the axially extending slot 198 between the first and second sidewalls 194, 196 of the wedge body 190. The spline tooth 226 can include a pair of opposing sidewalls 228, 230, with one of each of the opposing sidewalls 228, 230 positioned adjacent to the first and second sidewalls 194, 196, respectively, of the wedge body 190. Further, as shown in FIGS. 5, 6A and 6B, according to certain embodiments, the spline tooth 226 includes an inner wall 232 is configured to abut against the reference instrument 102. In the illustrated embodiment, the inner wall 232 is a curved surface that generally conforms to the shape of the adjacent surface of the reference instrument 102.

Figure 9:
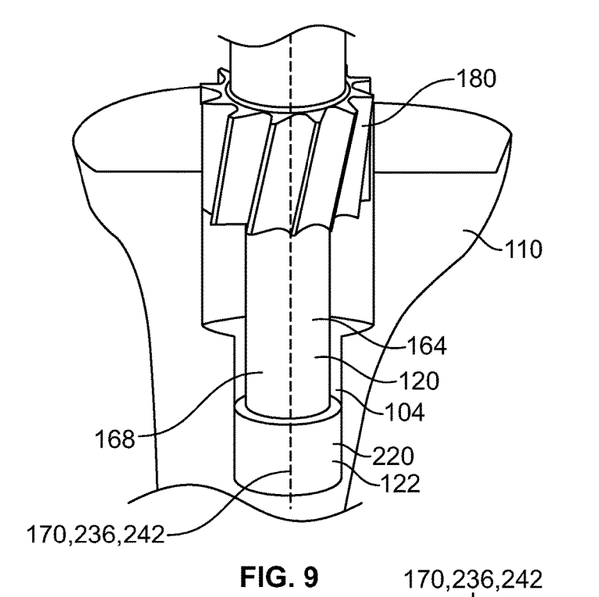
Figure 10:
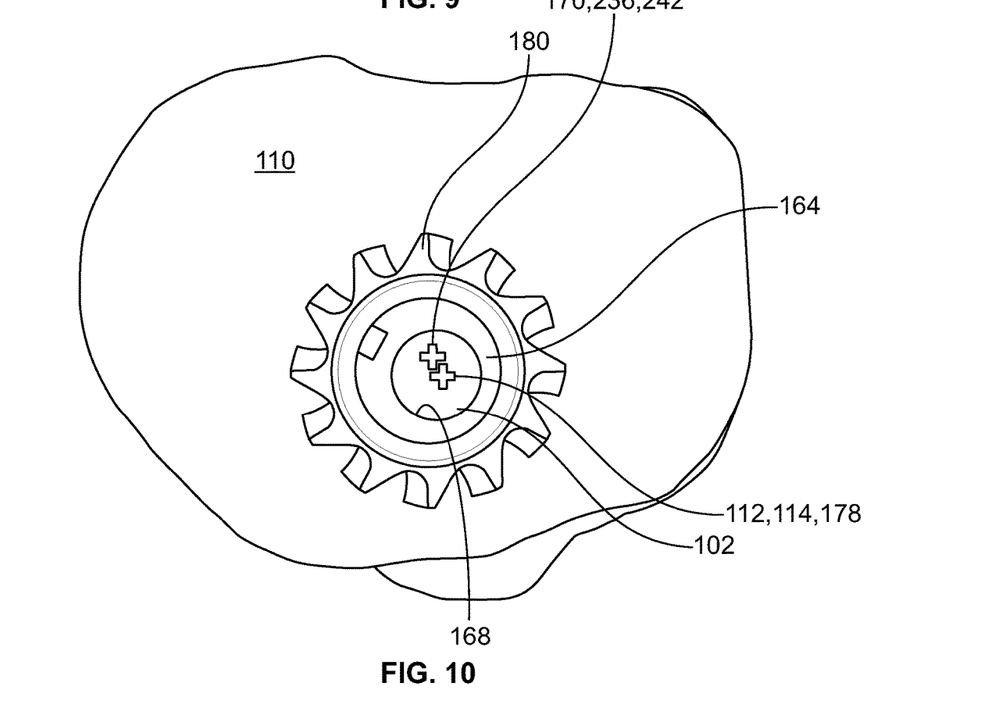
FIG. 10 illustrates a top view of the forming tool shown in FIG. 9 with generally common central axes of the reamer sleeve and the forming tool being offset from a central longitudinal axis of the reference instrument and/or of the canal of the bone.

The cap 122 further includes a groove 234 that extend into the inner side 218 of the cap wall 216. The groove 234 is configured to retain the retainer 210, such as, for example, a retaining clip, among other retainers. According to certain embodiments, the retainer 210 is a C-shaped retaining clip. Additionally, according to certain embodiments, the retainer 210 is configured to extend from about the first sidewall 194 to the second sidewall 196 of the wedge body 190, or in an area between the first and second sidewalls 194, 196. Additionally, the groove 234 can extend in a direction that is generally perpendicular to the direction of the tapered wall section 224 of the inner side 218 of the cap wall 216 and/or of the wedge surface 202 of the wedge body 190. Moreover, the groove 234 in the cap 122 can be non-perpendicular, and non-parallel to a central axis 236 of the cap 122. Further, the cap 122 can be positioned about the reamer sleeve 120 such that the central axis 236 of the cap 122 is generally aligned with the central longitudinal axis 170 of the reamer sleeve 120, as indicated by FIGS. 9 and 10.

The cap 122 can include opposing upper and lower walls 238, 240. The lower wall 240 can be configured to engage or abut against bone material in the intramedullary canal 104 or another opening in the bone 110. The upper wall 238 can be configured to engage the first end wall 102 of the reamer sleeve wall 164. Accordingly, the upper wall 238 of the cap 122 can extend at an incline that is generally parallel to the incline of the first end wall 192 of the reamer sleeve 120. Moreover, similar to the first end wall 192 of the reamer sleeve 120 and the groove 234 of the cap 122, the upper wall 238 of the cap 122 can extend along an incline that is generally perpendicular to the incline of the tapered wall section 224 of the inner side 218 of the cap wall 216 and/or of the wedge surface 202 of the wedge body 190. Thus, according to such an embodiment, the upper wall 238 of the cap 122 is non-perpendicular, and non-parallel to the central axis 236 of the cap 122.

During installation in a bone 110, the reamer sleeve 120 and cap 122 can be axially displaced along the reference instrument 102 and into the intramedullary canal 104 or other prepared opening in the bone 110. During at least the initial stages of installation, the cap 122 can be at a first position relative to the reamer sleeve 120, and moreover relative to the wedge body 190, as shown in FIG. 6A. With the cap 122 at the first position, the retainer 210 can be positioned adjacent to, and/or against the first shoulder 212 and within the cavity 208 of the wedge body 190. Axial displacement of the cap 122 and the reamer sleeve 120 into the intramedullary canal 104 or a prepared opening in the bone 110 can continue until the cap 122 encounters resistance, such as the lower wall 240 of the cap 122 abutting a portion of the bone 110, which precludes further axial displacement of the cap 122. While axial displacement of the cap 122 can stop, at least the reamer sleeve 120 can continue to be axially displaced. During such displacement, the wedge body 190 can continue to be displaced relative to, and/or against, both the tapered wall section 224 of the cap 122 and the reference instrument 102. During such displacement, the location of the retainer 210 within the cavity 208 of the wedge body 190 can change, as the second shoulder 214 of the cavity 208 can be moved into closer proximity to the retainer 210. Further, the relative position of the spline tooth 226 in the axially extending slot 198 between the first and second sidewalls 194, 196 of the wedge body 190 can change as axial displacement of the reamer sleeve 120 proceeds. Such axial displacement of the reamer sleeve 120 can continue until the wedge body 190 is at a second position relative to the tapered wall section 224. The reamer sleeve 120 can reach the second, wedge position when the wedge body 190 is slid to a position in which the perpendicular forces between the wedge body 190 and the tapered wall section 224, as well as the forces exerted on the wedge body 190 by the reference instrument 102, prohibit continued axial displacement of the reamer sleeve 120 relative to the cap 122. According to the illustrated embodiment, with the cap 122 at the second, wedged position relative to the reamer sleeve 120, the retainer 210 can be positioned within the cavity 208 in relative close proximity to the second shoulder 214, as shown by FIG. 6B. However, according to other embodiments, the distance between the retainer 210 and the second shoulder 214 can be adjusted by an increase in the distance between the first and second shoulders 212, 214.

With the cap 122 at the second position at least a portion of the first end wall 192 of the reamer sleeve 120 can be pressed against the adjacent upper wall 238 of the cap 122. Further, the degree to which the first end wall 192 of the reamer sleeve 120 abuts the upper wall 238 of the cap 122 can be enhanced by the first end wall 192 and the upper wall 238 each being configured to extend along similar inclines, and moreover inclines that are generally perpendicular to the inclined orientation of the tapered wall section 224 of the cap 122 and/or the wedge surface 202 of the wedge body 190, as previously discussed.

With the reamer sleeve 120 secured coupled to the cap 122, and with the cap 122 secured to the bone 110 and about the reference instrument 102, the guide 116 and guide bushing 118 can be removed from engagement with the reamer sleeve 120. Referencing FIGS. 8 and 9, with the guide 116 and guide bushing 118 removed, the forming tool 180 can be displaced along the reference instrument 102 and/or the reamer sleeve 120 until the forming tool 180 is positioned adjacent to the bone 110. As shown in FIGS. 9 and 10, with the forming tool 180 positioned about the reamer sleeve 120, a central axis 242 of the forming tool 180 can be generally aligned with, or at the same location, as the central longitudinal axis 170 of the reamer sleeve 120. Thus, in situations in which an offset reamer sleeve 120 is utilized, such as the reamer sleeve 120 illustrated in FIG. 10, the central axis 242 of the forming tool 180 can similarly be offset from a reference axis, such as, for example, offset from the longitudinal axis 178 of the inner passage 176 of the reamer sleeve 120, the central longitudinal axis 112 of the intramedullary canal 104, and/or the central longitudinal axis 114 of the reference instrument 102. Such a configuration can facilitate the formation of a formed portion of an opening in the bone 110 that has a selected degree of offset from at least the intramedullary canal 104, as depicted in FIG. 9. Moreover, as previously discussed, such offsetting can accommodate the central axis 242 of the forming tool 180 being offset along at least two axis relative to the intramedullary canal 104, as well as accommodate angular adjustment of such offsetting relative to at least the central longitudinal axis 112 of the intramedullary canal 104.

While the invention has been described in connection with what is presently considered to be the most practical and preferred embodiment, it is to be understood that the invention is not to be limited to the disclosed embodiment(s), but on the contrary, is intended to cover various modifications and equivalent arrangements included within the spirit and scope of the appended claims, which scope is to be accorded the broadest interpretation so as to encompass all such modifications and equivalent structures as permitted under the law. Furthermore it should be understood that while the use of the word preferable, preferably, or preferred in the description above indicates that feature so described may be more desirable, it nonetheless may not be necessary and any embodiment lacking the same may be contemplated as within the scope of the invention, that scope being defined by the claims that follow. In reading the claims it is intended that when words such as "a," "an," "at least one" and "at least a portion" are used, there is no intention to limit the claim to only one item unless specifically stated to the contrary in the claim. Further, when the language "at least a portion" and/or "a portion" is used the item may include a portion and/or the entire item unless specifically stated to the contrary.

The invention claimed is:

1. An apparatus, comprising:
   a reamer sleeve having a reamer wall and a wedge body, the reamer wall oriented about a central longitudinal axis, the reamer wall having an inner passage sized to receive insertion of a reference instrument structured for placement in a canal of a bone, the wedge body extending from a first end wall of the reamer wall, the wedge body having a wedge surface that extends axially in a direction arranged non-parallel and non-perpendicular to the central longitudinal axis; and
   a cap having an inner wall, at least a portion of the inner wall defines an opening of the cap sized to receive insertion of the wedge body, the inner wall having a tapered wall section that extends axially in a direction arranged generally parallel to the wedge surface; and
   wherein an outer side of the reamer wall is sized to be received within a portion of a forming tool adapted to remove bone material, wherein the cap and the reamer sleeve are adapted to be introduced in the canal of the bone, and wherein an outer side of the cap includes a plurality of radial protrusions configured to enhance engagement between the cap and the bone when the cap is introduced into the canal of the bone;
   wherein during an initial stage of installation, the cap has a first position relative to the reamer sleeve and the wedge body;
   wherein the reamer sleeve is adapted to be axially displaced relative to the cap with the wedge body having a second position relative to the tapered wall section of the cap, and wherein the reamer sleeve is adapted to be securely coupled to the cap in the second position; and
   wherein the first end wall of the reamer wall faces an upper wall of the cap and is operable to abut the upper wall of the cap to limit axial movement of the cap relative to the reamer sleeve.

2. The apparatus of claim 1, wherein the upper wall of the cap has an incline arranged generally perpendicular to the tapered wall section, and wherein the first end wall of the reamer wall has an incline arranged generally perpendicular to the wedge surface.

3. The apparatus of claim 2, wherein each of the inclines extends at an oblique angle relative to the central longitudinal axis.

4. The apparatus of claim 1, wherein the wedge surface extends between a first sidewall and a second sidewall, the first and second sidewalls separated at least by an axially extending slot.

5. The apparatus of claim 4, wherein the cap includes a spline tooth structured for placement in the axially extending slot.

6. The apparatus of claim 1, wherein the upper wall and the first end wall are helical.

7. The apparatus of claim 1, wherein the reamer wall has an outer diameter, wherein the opening of the cap has an inner diameter at the upper wall of the cap, and wherein the inner diameter of the opening is less than the outer diameter of the reamer wall such that the opening is inoperable to receive the reamer wall.

8. An apparatus, comprising:
a reamer sleeve having a reamer wall and a wedge body, the reamer wall oriented about a central longitudinal axis, the reamer wall having an inner passage sized to receive insertion of a reference instrument structured for placement in a canal of a bone, the wedge body extending from a first end wall of the reamer wall, the wedge body having a wedge surface that extends axially in a direction arranged non-parallel and non-perpendicular to the central longitudinal axis; and
a cap having an inner wall, at least a portion of the inner wall defines an opening of the cap sized to receive insertion of the wedge body, the inner wall having a tapered wall section that extends axially in a direction arranged generally parallel to the wedge surface;
wherein an outer side of the reamer wall is sized to be received within a portion of a forming tool adapted to remove bone material, and wherein the cap and the reamer sleeve are adapted to be introduced in the canal of the bone;
wherein during an initial stage of installation, the cap has a first position relative to the reamer sleeve and the wedge body;
wherein the reamer sleeve is adapted to be axially displaced relative to the cap with the wedge body having a second position relative to the tapered wall section of the cap, and wherein the reamer sleeve is adapted to be securely coupled to the cap in the second position; and
wherein the inner passage is centrally positioned about a longitudinal axis offset from the central longitudinal axis of the reamer wall.

9. An apparatus, comprising:
a reamer sleeve having a reamer wall and a wedge body, the reamer wall oriented about a central longitudinal axis, the reamer wall having an inner passage sized to receive insertion of a reference instrument structured for placement in a canal of a bone, the wedge body extending from a first end wall of the reamer wall, the wedge body having a wedge surface that extends axially in a direction arranged non-parallel and non-perpendicular to the central longitudinal axis; and
a cap having an inner wall, at least a portion of the inner wall defines an opening of the cap sized to receive insertion of the wedge body, the inner wall having a tapered wall section that extends axially in a direction arranged generally parallel to the wedge surface; and
a retainer structured to retain the cap in engagement with the wedge body, wherein the retainer comprises a C-shaped retaining clip;
wherein an outer side of the reamer wall is sized to be received within a portion of a forming tool adapted to remove bone material, and wherein the cap and the reamer sleeve are adapted to be introduced in the canal of the bone;
wherein during an initial stage of installation, the cap has a first position relative to the reamer sleeve and the wedge body;
wherein the first end wall of the reamer wall faces an upper wall of the cap and is operable to abut the upper wall of the cap to limit axial movement of the cap relative to the reamer sleeve.

10. The apparatus of claim 9, wherein the inner wall of the cap comprises a groove that receives the retainer.

11. The apparatus of claim 10, wherein the groove is oriented along an incline arranged generally perpendicular to the tapered wall section.

12. The apparatus of claim 10, wherein the wedge body further comprises a cavity sized to receive displaceable insertion of at least a portion of the retainer.

13. The apparatus of claim 10, wherein the groove is helical.

14. The apparatus of claim 10, wherein the retainer is captured between the wedge surface and the groove.

15. The apparatus of claim 4, wherein the wedge has a first end adjacent the first end wall of the reamer wall, wherein the wedge has a second end opposite the first end, and wherein the axially extending slot extends axially from the second end toward the first end.

16. An apparatus, comprising:
a reamer sleeve having a reamer wall and a wedge body, the reamer wall extending along a central longitudinal axis, the reamer wall defining an inner passage, the wedge body extending from a first end wall of the reamer wall, the wedge body having a wedge surface that extends axially in a direction arranged oblique to the central longitudinal axis; and
a cap having an inner wall, at least a portion of the inner wall defines an opening of the cap sized to receive insertion of the wedge body, the inner wall having a tapered wall section that extends axially in a direction arranged generally parallel to the wedge surface; and
wherein an outer side of the reamer wall is sized to be received within a portion of a forming tool adapted to remove bone material, and wherein the cap and the reamer sleeve are adapted to be introduced in a canal of a bone;
wherein during the cap has a first position relative to the reamer sleeve and the wedge body;
wherein the reamer sleeve is adapted to be axially displaced relative to the cap with the wedge body having a second position relative to the tapered wall section of the cap;
wherein the reamer sleeve is adapted to be securely coupled to the cap in the second position; and
wherein an outer side of the cap includes a plurality of radial protrusions configured to enhance engagement between the cap and the bone when the cap is introduced into the canal of the bone.

17. The apparatus of claim 16, wherein the radial protrusions are tapered.

18. The apparatus of claim 16, wherein the radial protrusions are configured to deform or compress when subjected to a radially-inward force.

19. The apparatus of claim 16, wherein the first end wall of the reamer wall faces an upper wall of the cap, wherein the reamer wall has an outer diameter, wherein the opening of the cap has an inner diameter at the upper wall of the cap, and wherein the inner diameter of the opening is less than the outer diameter of the reamer wall such that the opening is inoperable to receive the reamer wall.

20. The apparatus of claim 16, wherein the wedge body is asymmetrical about the central longitudinal axis.

* * * * *